United States Patent [19]

Mennel et al.

[11] Patent Number: 5,054,696

[45] Date of Patent: Oct. 8, 1991

[54] MEDICAL WASTE DISPOSAL SYSTEM

[75] Inventors: David B. Mennel, Greenwood; Joseph H. Wilson, Speedway; Martin E. Elliott, Indianapolis; Gary D. Gann, Greenwood, all of Ind.

[73] Assignee: Medical SafeTEC, Inc., Indianapolis, Ind.

[21] Appl. No.: 471,374

[22] Filed: Jan. 29, 1990

[51] Int. Cl.$^5$ .................... B02C 19/22; B01D 36/00
[52] U.S. Cl. .................... 241/34; 241/36; 241/99; 241/152 A; 241/248; 241/260.1; 241/DIG. 38; 210/173
[58] Field of Search ............ 241/37.5, 99, 186 A, 241/189 R, 260.1, 154, 152 A, 36, 248, 224, DIG. 38, 34; 210/173; 414/412

[56] References Cited

U.S. PATENT DOCUMENTS

| | | |
|---|---|---|
| 1,889,381 | 11/1932 | Rush . |
| 2,027,015 | 1/1936 | Bell . |
| 2,200,061 | 5/1940 | Green ..................... 241/260.1 X |
| 2,468,613 | 4/1949 | Bjorklund . |
| 2,985,211 | 5/1961 | Letz ..................... 241/248 X |
| 3,330,489 | 7/1967 | Worman . |
| 3,489,354 | 1/1970 | Harper et al. . |
| 3,596,842 | 8/1971 | Barber . |
| 3,721,183 | 3/1973 | Dunlea, Jr. . |
| 3,774,852 | 11/1973 | Edlund . |
| 3,834,630 | 9/1974 | Nelson ..................... 241/186 A X |
| 4,034,918 | 7/1977 | Culbertson et al. . |
| 4,040,571 | 8/1977 | Lindeborg . |
| 4,049,206 | 9/1977 | Koenig et al. . |
| 4,182,592 | 1/1980 | Henryson . |
| 4,253,615 | 3/1981 | Koenig ..................... 241/260.1 X |
| 4,509,700 | 4/1985 | Svengren . |
| 4,555,212 | 11/1985 | Jones . |
| 4,578,185 | 3/1986 | Wilson et al. . |
| 4,618,103 | 10/1986 | Wilson et al. . |
| 4,619,409 | 10/1986 | Harper et al. . |
| 4,641,792 | 2/1987 | Villavicencio et al. . |
| 4,844,363 | 7/1989 | Garnier et al. ..................... 241/224 |
| 4,852,817 | 8/1989 | Tipton ..................... 241/260.1 |
| 4,884,756 | 12/1989 | Pearson ..................... 241/99 X |

*Primary Examiner*—Mark Rosenbaum
*Attorney, Agent, or Firm*—Barnes & Thornburg

[57] ABSTRACT

A medical waste disposal system is provided for disposing of biologically contaminated waste material situated inside a rigid, form-stable container. The disposal system includes a processing unit for shredding the waste material into a shredded mass and for transporting the shredded mass into a disintegrator. The disintegrator mixes the shredded mass with a liquid disinfectant solution to disinfect the shredded mass and disintegrates the shredded mass into an unrecognizable particulate waste material.

23 Claims, 2 Drawing Sheets

MEDICAL WASTE DISPOSAL SYSTEM

BACKGROUND AND SUMMARY OF THE INVENTION

The present invention relates to a system for disposing of infectious, biologically contaminated waste material. More particularly, the present invention relates to a device for shredding, disintegrating, and disinfecting biologically contaminated waste products.

Examples of biologically contaminated waste products include hypodermic syringes, glassware, slides, gauze, needles, infectious tissues, blood-soaked materials, or other such potentially infected or contaminated waste materials typically generated during normal operation of a hospital. Public concern over the proper treatment and disposal of medical waste products has increased over the past several years. This increase is due in part to an increased public awareness of the diseases that can be transmitted by biologically contaminated waste products. It is therefore desirable to produce a disposal system which adequately disinfects and destroys medical waste products while minimizing the amount of contact between the medical waste products and an operator of the disposal system.

Various types of systems are known for disposing of medical waste products. On-site incinerators have been used in the past to dispose of such dangerous and infectious medical waste products. Incinerators which may be effective in decontaminating and reducing the size of the medical waste materials are not fully satisfactory because they require regular servicing and cleaning and provide some danger of toxic gas emissions. In recent years, systems have been developed to dispose of medical waste products without the use of such incinerators or other thermal devices.

It is known to provide devices which disintegrate medical waste products while mixing the waste products with liquid disinfectant solutions to produce a noninfectious and safely disposable particulate residue. One such known device provides a rotary hammermill which disintegrates medical waste products into a particulate form in the presence of a disinfectant. The solid particulate waste is then separated from the disinfectant solution by a suitable liquid-solid particle separator. Examples of such medical waste disposal systems are shown in U.S. Pat. Nos. 4,578,185; 4,618,103; and 4,619,409.

Problems still exist with these known nonthermal disposal systems. Even though these known systems effectively disinfect and destroy medical waste, operators of the systems still have substantial contact with medical waste products. Medical waste products generated by hospitals are typically stored inside rigid, self-supporting, form-stable containers. These containers are often made of a nonbreakable plastic material, but they may be made from any suitable material. The containers come in various shapes and sizes. The containers prevent leakage of fluids from inside the containers, and the rigid walls of the containers prevent needles, broken glass, or other articles from penetrating the container to isolate these medical waste products from hospital personnel. The containers typically have sealed lids to cover an opening of the container to prevent contact between hospital personnel and the medical waste products inside the containers.

To dispose of the medical waste products in the containers, an operator must typically dump the contents of the containers into the disposal system for processing. By removing the medical waste products from the containers, the operator is exposed to the infectious, contaminated medical waste material. This exposure increases the risk that the operator will be cut by glass products or punctured by syringe needles inside the container. The glass and needles inside the container are often covered with blood or other potentially harmful materials. Therefore, there is a risk that the operator may be infected by the contaminated medical waste products inside the container when disposing of the products by conventional methods.

One object of the present invention is to minimize the amount of contact between hospital personnel and biologically contaminated medical waste products produced by the hospital.

Another object of the present invention is to provide a disposal system for disinfecting and disposing of the entire contents of a rigid, self-supporting, form-stable container containing biologically contaminated waste products without requiring removal of the waste products from the container thereby preventing exposure of an operator of the disposal system to the potentially dangerous medical waste products.

Yet another object of the present invention is to dispose of the entire contents of a waste-filled container without the use of thermal processes.

According to the present invention, a waste disposal system for disposing of biologically contaminated waste material situated inside a self-supporting, form-stable container is provided. The system includes means for processing the entire container including an input for receiving the container, means for shredding the container and the waste material therein to form a shredded mass, and an output for discharging the shredded mass from the processing means. The shredding means feeds the shredded mass through the output of the processing means. The waste disposal system also includes means for disintegrating the shredded mass into a particulate waste material. The disintegrating means includes an input coupled to the output of the processing means for receiving the shredded mass from the output of the processing means.

In a preferred embodiment of the present invention, the processing means includes a trough portion formed to include an input for receiving the waste-filled container and an output aperture for discharging the shredded mass from the trough portion. The processing means includes a rotatable auger screw having a proximal end, a distal end, and an axis of rotation. The auger screw is situated inside the trough portion for shredding the waste-filled container into the shredded mass and for transporting the shredded mass in a direction along the axis of rotation toward the output aperture of the trough portion to discharge the shredded mass from the trough portion. The processing means also includes means coupled to the proximal end of the auger screw for rotating the auger screw in a predetermined direction about its axis of rotation.

Hopper means is provided for defining an enclosed housing coupled to the input of the trough portion. The hopper means includes input means for receiving the container inside the enclosed housing. The processing means further includes ram means situated inside the hopper means for applying a biasing force to the container to force the container against the auger screw and to retain the container in engagement with the auger screw until the auger screw shreds the entire container into the shredded mass.

The hopper means includes a door for covering the input means movable between an open position to permit the container to be loaded into the hopper means and a closed position for sealing the input means after the container is positioned within the hopper means. The processing means further includes means for disabling the ram means and the rotating means when the door is in the open position to prevent an operator from being injured by either the ram means or the rotating auger screw.

In one preferred embodiment, the ram means includes a plunger situated inside the hopper means for engaging the container and means interconnecting the plunger and the hopper means for providing reciprocating movement of the plunger from a first position to permit the container to be loaded into the hopper means and a second position to force the container into engagement with the auger screw to shred the container. The reciprocating means can include a pneumatically controlled air cylinder situated inside the hopper means. The air cylinder is movable from a retracted position defining the first position of the plunger to an extended position defining the second position of the plunger.

The processing means can also include means for providing a liquid disinfectant solution to the trough portion to clean the auger screw and to treat the shredded mass with the liquid disinfectant solution. Exhaust means coupled to the hopper means can also be included for providing a negative pressure inside the hopper means during operation of the auger screw to vent the hopper means and the trough portion of the system while shredding the container. The exhaust means prevents contaminated air from escaping from within the hopper means into the surrounding atmosphere while shredding the container. The exhaust can be filtered to remove contaminants from the exhaust.

The processing means can also include a gate region between the trough portion and the hammermill which includes a reciprocating plate member for opening and closing the gate region. When the door to the hopper is open, plate member blocks the gate region to prevent small particles escaping from the hammermill from passing upwardly through the trough portion and through the opening in the hopper.

A system computer is used to synchronize and control the means for rotating the auger screw, the ram means, the exhaust means, the supply of disinfectant solution to the trough portion, and the movement of the plate member.

One feature of the present invention is the provision of a processing unit including an auger screw for shredding a container filled with waste material into a shredded mass and for feeding the shredded mass into a disintegrator for disintegrating the shredded mass into a particulate waste product. Advantageously, such a feature permits an entire rigid, form-stable container to be processed and sanitized without removing biologically contaminated waste material from the container to prevent contact between the contaminated waste material and an operator of the disposal device. This feature reduces the risk of injury to the operator and reduces the risk of exposing the operator to the infectious contaminated medical waste products situated inside the containers.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
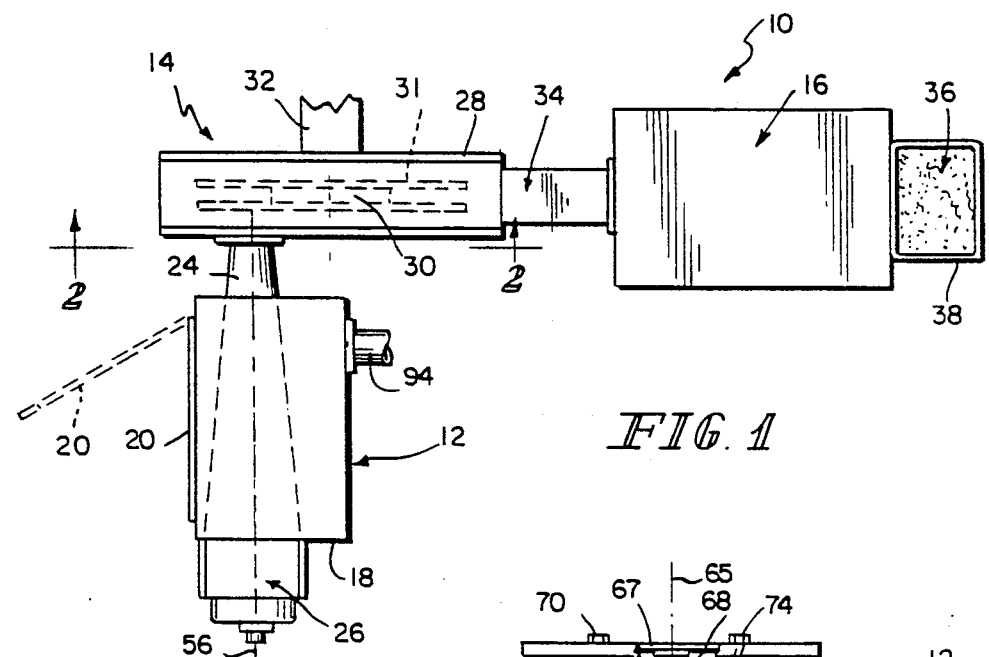
FIG. 1 is a plan view of a preferred embodiment of the medical waste disposal system of the present invention illustrating a container processing unit for shredding an entire container filled with medical waste products, a hammermill for disinfecting and disintegrating the shredded container and the medical waste products therein into a particulate waste material, and a liquid-solid particle separator for separating the particulate waste material from a liquid disinfectant solution.
Figure 2:
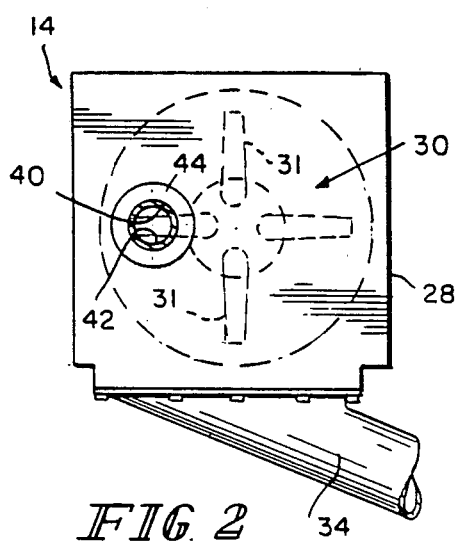
FIG. 2 is a sectional view taken along lines 2—2 of FIG. 1 illustrating the input port of the hammermill coupled to the output of the processing unit.

Referring now to the drawings, FIG. 1 illustrates a preferred embodiment of a medical waste disposal system 10 of the present invention. The disposal system 10 is designed to destroy and disinfect an entire, rigid, self-supporting, form-stable container 50 (see FIG. 3) containing biologically contaminated medical waste products (not shown). The containers 50 typically are made of plastic or other suitable materials and come in various sizes.

Disposal system 10 includes a container processing unit 12 for shredding, shearing, or bursting the container 50 to reduce the cross-sectional area of the container 50. Processing unit 12 transports the shredded mass comprising the torn-apart container 50 and any waste products contained therein into a disintegrator such as hammermill 14. The cross-sectional area of the container 50 and the waste products therein must be reduced to a size capable of passing through a circular inlet aperture of hammermill 14 typically having a diameter of 5½ inches or less.

Hammermill 14 mixes the shredded mass inside hammermill 14 with a disinfectant solution and disintegrates the shredded mass into a particulate waste material. The mixture comprising particulate waste material and disinfectant solution exits the hammermill 14 through apertures (not shown) formed in the bottom of casing 28 and enters transmission chute 34. The solid particulate waste material and disinfectant solution mixture then passes through chute 34 into a liquid-solid particle separator 16.

Container processing unit 12 includes a hopper 18 for receiving the entire container 50. Hopper 18 is sealed by a door 20 movable from a first closed position abutting hopper 18 to a second open position shown in phantom in FIG. 1. As discussed in detail below, container processing unit 12 bursts, tears, shears, or shreds container 50 when the door 20 is in the closed position to produce the shredded mass which is transported through output region 24 and into hammermill 14.

Hammermill 14 includes a rotating hammer assembly 30 having a plurality of hammer elements 31 which are rotated by a drive shaft 32. The hammermill 14 rotates the hammer elements 31 at high speeds, for example, on the order of 3500 rpm. The hammer elements 31 strike the shredded mass, breaking it into small pieces creating a particulate waste material inside the hammermill 14. After hammer elements 31 repeatedly strike the shredded mass, the shredded mass is disintegrated into particulate waste material. The particulate waste material is reduced to a size small enough to pass through apertures (not shown) in the bottom of casing 28 of hammermill 14. The apertures typically have a diameter of about ½ inch or less.

It is understood that any type of disintegrator may be used with the disposal system 10 of the present invention as long as the disintegrator provides an unrecognizable particulate waste product which is completely disinfected and may be safely disposed of in a conventional manner.

A liquid disinfectant solution is mixed with the shredded mass inside hammermill 14. Solid particulate waste material exiting hammermill 14 along with the liquid disinfectant solution passes through transmission chute 34 to liquid-solid particle separator 16. In the preferred embodiment, liquid-solid particle separator 16 includes sieve conveyor (not shown) that transports the mixture of particulate waste material and disinfectant solution upwardly through the separator 16 as discussed in detail in U.S. Pat. No. 4,578,185. The solid particulate waste 36 remains on the conveyor sieve and is transported into a container 38 while the liquid disinfectant falls through the conveyor. The particulate waste 36 is non-infectious and may be safely disposed of in a conventional manner.

Hammermill 14 includes a vacuum ventilation means (not shown) for providing a negative pressure inside hammermill 14 to prevent the release of potentially dangerous microbial aerosols or other contamination from hammermill 14 during treatment and disposal of the waste articles within the hammermill 14. Filters can be included in the ventilation means to filter the mists, vapors, particles, etc. contained in the exhaust from hammermill 14.

Figure 3:
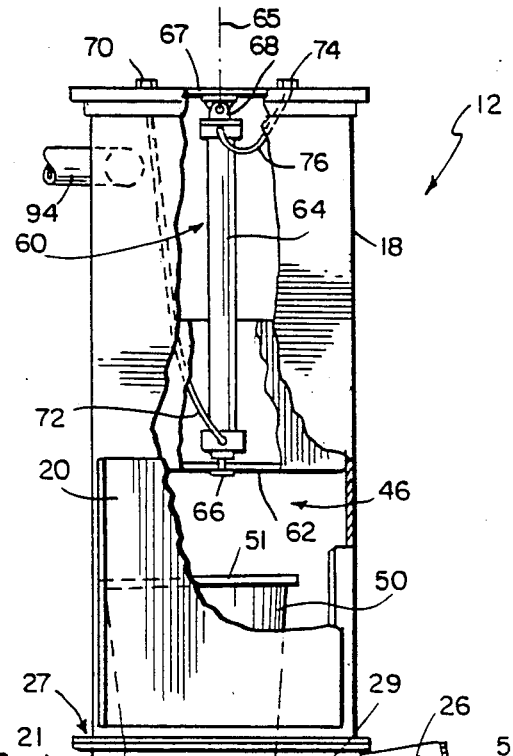
FIG. 3 is a front elevational view of the processing unit with portions broken away illustrating the position of a ram mechanism above an input region of a hopper and an auger screw situated inside a trough portion for shredding the entire container and any medical waste products therein into a shredded mass and transporting the shredded mass along an axis of rotation of the auger screw through the output of the trough portion and into the hammermill for disintegrating the shredded mass.
Figure 3:
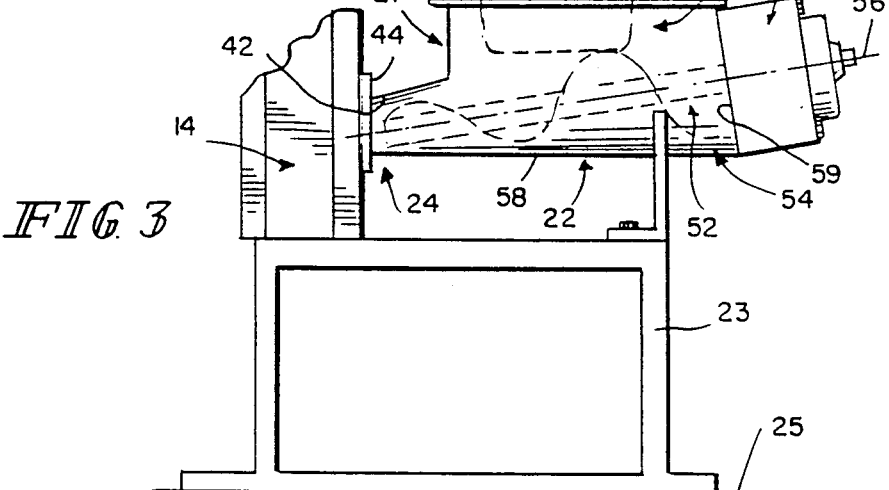
Figure 4:
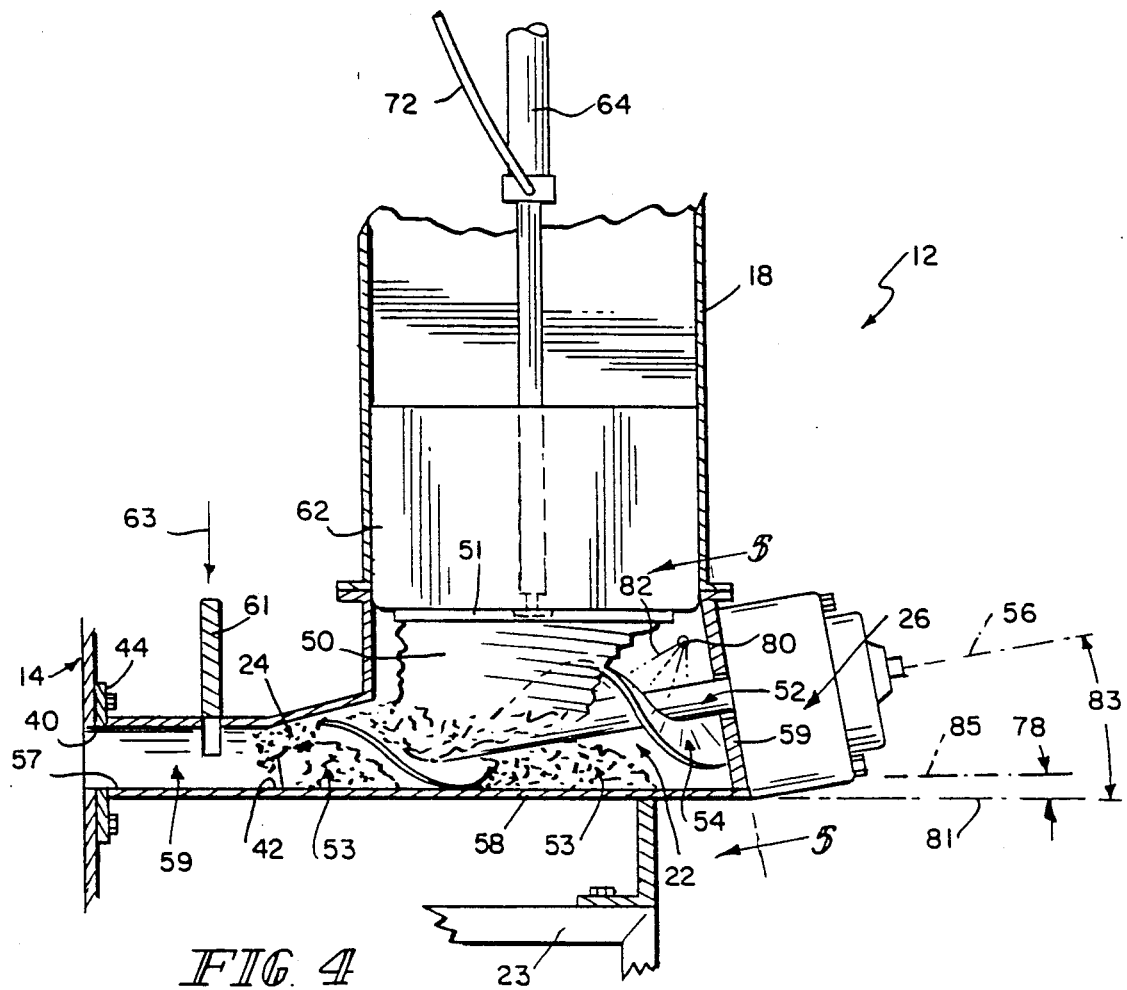
FIG. 4 is a transverse sectional view taken through a portion of the processing unit illustrating the plunger in its extended position to force the container into engagement with the auger screw to shred the container to form the shredded mass and illustrating an optional gate region coupled to the input of the hammermill.
Figure 5:
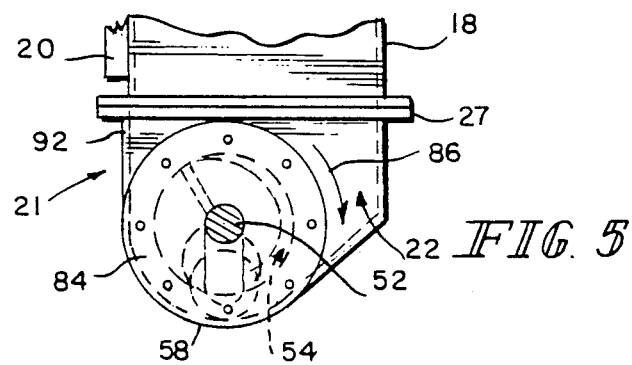
FIG. 5 is a sectional view taken along lines 5—5 of FIG. 4 illustrating the position of the auger screw inside the trough portion and illustrating the dimensions of the shredding region of the trough portion.

The container processing unit 12 of the present invention is more particularly shown in FIGS. 3-5. FIG. 3 illustrates the processing unit 12 which includes a hopper 18, a trough portion 21, and a support stand 23 for supporting the processing unit above floor 25. Trough portion 21 includes an input region 29 for receiving the rigid, form-stable container 50, a shredding region 22 for bursting and tearing the waste-filled container 50 into a shredded mass, and an output region 24 for discharging the shredded mass from trough portion 21. Hopper 18 is coupled to the input region 29 of trough portion 21 as shown at location 27.

An auger screw 54 including a drive shaft 52 having an axis of rotation 56 is situated within the trough portion 21. A proximal end of auger screw 54 is coupled to a gear reducer 26 situated on an end wall 59 of trough portion 21. Drive shaft 52 of auger screw 54 extends away from end wall 59 in a direction toward outlet region 24 of trough portion 21. A distal end of auger screw 54 lies within the output region 24 of trough portion 21 in close proximity to an outlet aperture 42 of trough portion 21. A motor drives gear reducer 26 to rotate auger screw 54 in a predetermined direction about its axis of rotation 56.

Hopper 18 is formed to include an input region or opening 46 for receiving waste-filled containers 50 inside the hopper 18. Container 50 is formed to include a lid portion 51 for sealing the container to prevent exposure of an operator to the medical waste products inside container 50. Door 20 seals the input region 46 of hopper 18 after container 50 has been loaded into hopper 18.

After container 50 is loaded into hopper 18, the motor 26 is activated to rotate auger screw 54 and a ram mechanism 60 is activated to force container 50 into engagement with auger screw 54. Rotation of auger screw 54 bursts, tears, or shreds the container into a shredded mass 53 (see FIG. 4) and transports the shredded mass 53 along the axis of rotation 56 of auger screw 54 through output region 24 and into hammermill 14. Ram assembly 60 includes a plunger 62 for engaging the container 50 and an air cylinder 64 coupled to plunger 62 for providing reciprocating movement of plunger 62 along the longitudinal axis 65 of the enclosed housing defined by hopper 18. One end of air cylinder 64 is coupled to a top support 67 of hopper 18. The second end of air cylinder 64 is connected to plunger 62 by connector 66. Hopper 18 includes an air inlet 70 coupled to an air supply hose 72 for supplying air to air cylinder 64. Hopper 18 also includes an air outlet 74 coupled to air cylinder 64 by hose 76. Inlet port 70 and outlet port 74 operate two control reciprocating movement of air cylinder 64 from a retracted position shown in FIG. 3 to an extended position shown in FIG. 4. Operation of a valve (not shown) controlling movement of the air cylinder is controlled by a system computer (not shown).

It is understood that various methods may be used to provide reciprocating movement of plunger 62. A scissor jack mechanism, chain drive mechanism, worm gear mechanism, or other type device coupled to hopper 18 in various ways could be used to provide reciprocating movement of plunger 62.

FIG. 4 illustrates the container 50 and the waste products contained therein being bursted, torn, sheared, or shredded by auger screw 54 inside shredding region 22 of trough portion 21. A shredded mass 53 which includes the container 50 and the medical waste products situated inside container 50 is formed in shredding region 22 and is transported by auger screw 54 through outlet region 24 of trough portion 21 along axis rotation 56 of auger screw 54.

The embodiment of the processing unit 12 shown in FIG. 4 illustrates an optional gate region 59 which may be included on processing unit 12. Outlet region 24 of trough portion 21 is coupled to gate region 59. Gate region 59 includes a plate member 61 which acts as a guillotine-type door movable between first and second positions to open and close gate region 59. When plate member 61 is in the first position shown in FIG. 4, the shredded mass 53 can be transported through gate region 59 to hammermill 14. When plate member 61 moves downward in the direction of arrow 63 to the dotted position, gate region 59 is blocked by plate member 61. Gate region 59 is coupled to an inlet 40 of hammermill 14 by a suitable connecting plate 44. Therefore, outlet aperture 57 of gate region 59 communicates with inlet aperture 40 of hammermill 14. Because hammermill 14 continues to run while the operator loads a new container 50 into hopper 18, it is possible that small particles can be ejected from hammermill 14. These small particles may pass through trough portion 21 and out opening 46 of hopper 18. Therefore, plate member 61 is moved to the second position to block gate region 59 to prevent particles from escaping from hammermill 14 when door 20 of hopper 18 is in its open position.

Trough portion 21 is formed to include a liquid disinfectant inlet aperture 80 situated in close proximity to inlet 29 and end wall 59 of trough portion 21. The processing unit 18 includes means for supplying a stream of liquid disinfectant solution 82 through the aperture 80 to clean auger screw 54 and to treat shredded mass 53 with the liquid disinfectant solution before the shredded mass 53 enters hammermill 14.

As illustrated in FIG. 4, bottom wall 58 of trough portion 21 is aligned at a predetermined, non-parallel angle 78 with respect to a horizontal plane 81 parallel to the floor or support surface 25. Line 85 represents the plane of bottom wall 58. Preferably, angle 78 is about 2 degrees. By aligning bottom wall 58 of trough portion 21 at angle 78, a downhill slope is provided to transport the liquid disinfectant solution along with any liquids contained in container 50 from the trough portion 21 to hammermill 14. Auger screw 54 is also aligned so that the axis of rotation 56 of auger screw 54 is aligned at a second predetermined, non-parallel angle 83 with respect to horizontal plane 81. By positioning the proximal end of auger screw 54 above the distal end of the auger screw 54, transporting the shredded mass 53 toward outlet aperture 42 of trough portion 21 is facilitated. Angle 83 is greater than angle 78.

The cross-sectional area of trough portion 21 is illustrated in FIG. 5. Auger screw 54 is situated inside shredding region 22 in close proximity to front wall 92. During normal operation, drive shaft 52 of auger screw 54 is rotated in a forward or clockwise direction 86. Rotation of auger screw 54 in direction 86 forces the container 50 against back wall 90 and bottom wall 58 while the auger screw 54 bursts and tears or shreds the waste-filled container 50. The direction of rotation of auger screw 54 is reversible to loosen lodged material from auger screw 54 to aid the shredding of container 50. Auger screw 54 is preferably rotated at a speed of less than about 20 rpm.

During the processing of container 50, it is desirable to provide an exhaust system for providing a negative pressure inside hopper 18 to vent hopper 18 and trough portion 21. An exhaust port 94 shown in FIG. 3 may be positioned at any location on the hopper 18 to ventilate hopper 18 while processing container 50. Exhaust port 94 is connected to the exhaust system of hammermill 14 and can be filtered to remove contaminants from the exhaust. The exhaust system prevents the escape of potentially dangerous microbial aerosols and other contamination from hopper 18 while processing container 50.

Door 20 of hopper 18 must be in the closed position to seal input region 46 of hopper 18 before the ram mechanism 60 or the gear reducer 26 can be activated to process container 50. By disabling ram mechanism 60 and gear reducer 26 when the door 20 is in the open position, the present invention reduces the possibility that an operator will be injured by the ram assembly 60 or the auger screw 54.

During operation of the waste disposal system 10, an operator opens door 20 of hopper 18 and loads a waste-filled container 50 into input region 46 of hopper 18. While the door 20 is open, plate member 61 blocks gate region 59 to prevent particulate waste products escaping from hammermill 14 from passing upwardly through trough portion 21 and through opening 46 of hopper 18. The operator then closes and latches door 20 to seal the enclosed interior region of hopper 18. After door 20 is closed, plate member 61 moves upwardly to open gate region 59. The motor driving gear reducer 26 is activated to begin rotating auger screw 54 in a predetermined direction about its axis of rotation 56. Ram mechanism 60 is also activated so that air cylinder 64 moves from its retracted position shown in FIG. 3 to its extended position shown in FIG. 4 to move the container 50 along the longitudinal axis 65 of the input channel defined by hopper 18.

Plunger 62 engages container 50 and forces container 50 against auger screw 54. Plunger 62 continues to apply force against container 50 to retain container 50 in engagement with auger screw 54 until the entire container 50 is torn into the shredded mass 53 in shredding region 22 of trough portion 21. Plunger 62 may be reciprocated multiple times while processing container 50 to help the auger screw 54 process or shred the entire container 50. Shredded mass 53 is then transported by auger screw 54 in a direction along its axis of rotation 56 through outlet region 24 of trough portion which surrounds the distal end of tapered auger screw 54. The shredded mass 53 is then fed through gate region 59 and into hammermill 14. While the auger screw 54 tears and reduces the cross-sectional area of container 50, a stream of liquid disinfectant solution 82 is supplied through aperture 80 in trough portion 21 to clean auger screw 54 and to treat shredded mass 53 with the disinfectant solution. A system computer (not shown) controls and synchronizes the operation of processing unit 12.

Once inside hammermill 14, hammer elements 31 disintegrate the shredded mass 53. During this disintegration process, the shredded mass 53 is further treated with disinfectant solution. The liquid disinfectant solution and the particulate material are discharged through apertures in the bottom of hammermill 14 and are transported through transmission chute 34 to liquid-solid particle separator 16. Liquid-solid particle separator 16 separates the particulate waste material from the liquid disinfectant solution and deposits the solid particulate material 36 into a suitable container 38 for disposal. The particulate waste material 36 is non-infectious and can be safely disposed of in a conventional manner.

Although the invention has been described in detail with reference to a preferred embodiment, variations and modifications exists within the scope and spirit of the invention as described and defined in the following claims.

What is claimed is:

1. A waste disposal system for disposing of biologically contaminated waste material situated inside a self-supporting, form-stable container, the system comprising means for processing the entire container and any waste material therein, the processing means including an input for receiving the container, means for shredding the container and the waste material therein to form a shredded mass, and an output for discharging the shredded mass from the processing means, the shredding means feeding the shredded mass through the output of the processing means, means for disintegrating the shredded mass into a particulate waste material, the disintegrating means including an input coupled to the output of the processing means for receiving the shredded mass from the output of the processing means, wherein the shredding means includes a trough portion and a rotatable auger screw situated within the trough portion for shredding the container into the shredded mass, the trough portion including an output opening coupled to the input of the disintegrating means.

2. The system of claim 1, further comprising means for supplying a liquid disinfectant solution to the trough portion to treat the shredded mass with the liquid disinfectant solution before the shredded mass enters the disintegrating means.

3. The system of claim 1, wherein the auger screw has a proximal end portion and a distal end portion and the trough portion includes a shredding region and an output region, the output region having a first end coupled to the shredding region and a second end coupled to the disintegrating means, the output region surrounding the distal end portion of the auger screw.

4. The system of claim 3, wherein the output region has a decreasing cross-sectional area along the axis of rotation of the auger screw in a direction from the first end to the second end of the output region.

5. A waste disposal system for reducing the cross-sectional area of a rigid, form-stable container containing biologically contaminated waste into a shredded mass which is then inserted into a disintegrator, the system comprising a trough portion formed to include an input means for receiving the waste-filled container and an output aperture for discharging the shredded mass from the trough portion, a rotatable auger screw having a proximal end, a distal end, and an axis of rotation, the auger screw being situated inside the trough portion for shredding the waste-filled container and contaminated waste therein into a shredded mass and for transporting the shredded mass in a direction along the axis of rotation toward the output aperture of the trough portion to discharge the shredded mass from the trough portion into a disintegration means for disintegrating the shredded mass, means coupled to the proximal end of the auger screw for rotating the auger screw in a predetermined direction about its axis of rotation, a hopper including an outer side wall defining an elongated container input channel having a longitudinal axis therethrough, the side wall being formed to include an input opening for loading the container into the hopper, means for coupling the hopper to the input means of the trough portion to align the longitudinal axis of the input channel substantially perpendicularly to the axis of rotation of the auger screw, and means for moving the container along the longitudinal axis of the input channel toward the auger screw to force the container against the auger screw and to retain the container in engagement with the auger screw until the entire container is shredded.

6. The system of claim 5, wherein the container moving means includes a plunger situated inside the hopper for engaging the container and means interconnecting the plunger and the hopper for providing reciprocating movement of the plunger along the longitudinal axis of the input channel from a first position to permit the container to be loaded into the hopper and a second position to force the container into engagement with the auger screw.

7. The system of claim 6, wherein the reciprocating means includes a pneumatically controlled air cylinder, the air cylinder being movable from a retracted position defining the first position of the plunger and an extended position defining the second position of the plunger.

8. A waste disposal system for disposing of biologically contaminated waste material situated inside the self-supporting, form-stable container, the system comprising a trough portion formed to include an input and an output, a rotatable auger screw having a proximal end, a distal end, and an axis of rotation, the auger screw being situated inside the trough portion for tearing the container to reduce the cross-sectional area of the waste-filled container to form a shredded mass of the container and waste material contained therein and for transporting the shredded mass in a direction along the axis of rotation toward the output of the trough portion to discharge the shredded mass from the output of the trough portion, means coupled to the proximal end of the auger screw for rotating the auger screw in a predetermined direction about its axis of rotation, a rotary hammermill for disintegrating the shredded mass into particulate waste material, the hammermill including an input coupled to the output of the trough portion for receiving the shredded mass from the trough portion, means coupled to the input of the trough portion for receiving the waste-filled container, and means situated inside the container receiving means for forcing the container against the auger screw to shred the container and contaminated waste into a shredded mass and to retain the container and waste in engagement with the auger screw until the entire container and waste is shredded into the shredded mass.

9. The system of claim 8, further comprising a gate region situated between the output of the trough portion and the input of the rotary hammermill, and a reciprocating plate member movable from a first position for opening the gate region to permit the shredded mass to pass from the trough portion to the hammermill and a second closed position to block the gate region to prevent particulate waste material escaping from the hammermill from passing through the gate region.

10. The system of claim 9, wherein the container receiving means is formed to include an input opening and a door movable from an open position to permit the container to be loaded into the input opening and a closed position for sealing the input opening while processing the container, and the plate member is situated in the first position when the door is in the closed position and the plate member is situated in the second position when the door is in the open position.

11. A waste disposal system for shredding biologically contaminated waste situated inside a rigid, form-stable container into a shredded mass which is then inserted into a disintegrator, the system comprising a trough portion formed to include an input for receiving the waste-filled container and an output aperture for discharging the shredded mass from the trough portion, a rotatable auger screw having a proximal end, a distal end, and an axis of rotation, the auger screw being situated inside the trough portion for shredding the waste-filled container along with the waste situated inside of the container into a shredded mass and for transporting the shredded mass in a direction along the axis of rotation toward the output aperture of the trough portion to discharge the shredded mass from the trough portion, disintegrator means receiving the shredded mass from the output aperture for disintegrating the shredded mass, means coupled to the proximal end of the auger screw for rotating the auger screw in a predetermined direction about its axis of rotation, hopper means defining an enclosed housing coupled to the input of the trough portion, the hopper means including input means for receiving the container inside the enclosed housing, and ram means situated inside the hopper means for applying a biasing force to the container to force the container against the auger screw and to retain the container in engagement with the auger screw until the auger screw shreds the entire container and the waste situated therein into the shredded mass.

12. The system of claim 11, wherein the trough portion includes a shredding region and an output region, the output region having a first end coupled to the shredding region and a second end defining the output aperture of the trough portion, the output region of the trough portion surrounding the distal end of the rotatable auger screw.

13. The system of claim 12, wherein the output region has a decreasing cross-sectional area along the axis of rotation of the auger screw in a direction from the first end to the second end of the output region to regulate the output feed rate of the shredded mass through the output aperture of the trough portion.

14. The system of claim 11, wherein the proximal end of the auger screw is coupled to the trough portion in close proximity to the inlet and the distal end of the auger screw is situated in close proximity to the outlet aperture of the trough portion, and the diameter of the auger screw about the axis of rotation decreases from the proximal end to the distal end of the auger screw.

15. The system of claim 14, wherein the auger screw is aligned to position the proximal end of the auger screw above the distal end of the auger screw to facilitate transporting the shredded mass through the trough portion toward the outlet aperture.

16. The system of claim 11, wherein the hopper means includes a door for covering the input means movable between an open position to permit the container to be loaded into the hopper means and a closed position for sealing the input means after the container is positioned within the hopper means, the system further comprising means for disabling the ram means and the rotating means when the door is in the open position.

17. The system of claim 11, wherein the ram means includes a plunger situated inside the hopper means for engaging the container and means interconnecting the plunger and the hopper means for providing reciprocating movement of the plunger from a first position to permit the container to be loaded into the hopper means and a second position to force the container into engagement with the auger screw to shred the container.

18. The system of claim 17, wherein the reciprocating means includes a pneumatically controlled air cylinder, the air cylinder being movable from a retracted position defining the first position of the plunger and an extended position defining the second position of the plunger.

19. The system of claim 11, further comprising exhaust means coupled to the hopper means for providing a negative pressure inside the hopper means during operation of the auger screw to vent the hopper means and the trough portion of the system while shredding the container.

20. The system of claim 19, wherein the exhaust means includes means for filtering the exhaust passing through the exhaust means.

21. The system of claim 11, further comprising means for providing a liquid disinfectant solution to the trough portion to clean the auger screw and to treat the shredded mass with the liquid disinfectant solution.

22. The system of claim 21, wherein the trough portion includes a bottom surface aligned at a predetermined, nonparallel angle with respect to a horizontal plane to provide a downhill grade toward the output aperture of the trough portion to discharge the liquid disinfectant solution from the trough portion.

23. The system of claim 21, wherein the means for providing the liquid disinfectant solution includes an aperture formed in close proximity to the inlet of the trough portion above the proximal end of the auger screw and means for supplying a stream of the liquid disinfectant solution through the disinfectant supply aperture.

* * * * *